United States Patent
Fournie

(10) Patent No.: US 11,069,096 B2
(45) Date of Patent: Jul. 20, 2021

(54) METHOD FOR PROCESSING PARAMETERS OF A MACHINE LEARNING METHOD AND RECONSTRUCTION METHOD

(71) Applicant: Siemens Healthcare GmbH, Erlangen (DE)

(72) Inventor: Eric Fournie, Erlangen (DE)

(73) Assignee: SIEMENS HEALTHCARE GMBH, Erlangen (DE)

(*) Notice: Subject to any disclaimer, the term of this patent is extended or adjusted under 35 U.S.C. 154(b) by 90 days.

(21) Appl. No.: 16/354,498

(22) Filed: Mar. 15, 2019

(65) Prior Publication Data
US 2019/0295294 A1   Sep. 26, 2019

(30) Foreign Application Priority Data

Mar. 23, 2018   (EP) ..................... 18163687

(51) Int. Cl.
*G06K 9/00*   (2006.01)
*G06T 11/00*   (2006.01)
(Continued)

(52) U.S. Cl.
CPC ............ *G06T 11/003* (2013.01); *A61B 6/032* (2013.01); *A61B 6/503* (2013.01); *A61B 6/5205* (2013.01);
(Continued)

(58) Field of Classification Search
CPC .................................................. G06T 11/003
See application file for complete search history.

(56) References Cited

U.S. PATENT DOCUMENTS 8,224,056 B2   7/2012   Pack
2010/0195888 A1   8/2010   Bruder
(Continued)

FOREIGN PATENT DOCUMENTS

DE   102009007236 A1   8/2010
DE   102011007529 A1   10/2012
(Continued)

OTHER PUBLICATIONS

Tang, Quiulin et al.: "A fully four-dimensional; iterative motion estimation and compensation method for cardiac CT"; in: Med. Phys.; vol. 39, No. 7; pp. 4291-4305; 2012;.
(Continued)

*Primary Examiner* — Oneal R Mistry
(74) *Attorney, Agent, or Firm* — Harness, Dickey & Pierce, P.L.C.

(57) ABSTRACT

A method is for processing parameters of a machine-learning method for providing a correction dataset for motion correction of a CT image dataset of an object that moves during recording thereof. A training dataset with a number of reference image datasets for introduction into the machine-learning method is provided. Iteration is performed. In each of the iteration steps, a correction dataset is determined for each of the reference image datasets via the machine-learning method and a result of a cost function dependent on the correction datasets determined in this iteration step is ascertained. The iteration is terminated or a parameter of the machine-learning method is altered in dependence on the result of the cost function. A reconstruction method further uses the processed machine-learning method.

11 Claims, 5 Drawing Sheets

(51) Int. Cl.
- *G06T 7/00* (2017.01)
- *A61B 6/00* (2006.01)
- *A61B 6/03* (2006.01)
- *G06N 3/04* (2006.01)
- *G06N 3/08* (2006.01)

(52) U.S. Cl.
CPC ......... *A61B 6/5264* (2013.01); *G06N 3/0454* (2013.01); *G06N 3/08* (2013.01); *G06T 7/0012* (2013.01); *G06T 11/006* (2013.01); *G06T 2207/10072* (2013.01); *G06T 2207/20081* (2013.01); *G06T 2207/20084* (2013.01)

(56) References Cited

U.S. PATENT DOCUMENTS

| | | | |
|---|---|---|---|
| 2016/0000383 | A1 | 1/2016 | Lee et al. |
| 2018/0268255 | A1* | 9/2018 | Surazhsky ............ G06N 3/0454 |
| 2019/0108441 | A1* | 4/2019 | Thibault ................ G06N 20/00 |
| 2019/0108904 | A1* | 4/2019 | Zhou ...................... G06K 9/66 |
| 2019/0277935 | A1* | 9/2019 | Zeng ...................... G06N 5/046 |

FOREIGN PATENT DOCUMENTS

| | | |
|---|---|---|
| DE | 102011083647 A1 | 3/2013 |
| WO | WO 2017223560 A1 | 12/2017 |

OTHER PUBLICATIONS

Van Stevendaal, U. et al.:"A motion-compensated scheme for helical cone-beam reconstruction in cardiac CT angiography,"; in Medical Physics; vol. 35; Issue 7; pp. 3239-3251; Jul. 2008; DOI: 10.1118/1.2938733; 2008.

Hahn, Juliane et al.: "Reduction of Motion Artifacts in Cardiac CT based on Partial Angle Reconstructions from Short Scan Data"; in: Medical Imaging; Siemens Healthcare GmbH 1. Power Point Präsentation; 2. publication Physics of Medical Imaging; Feb. 27-Mar. 3, 2016; San Diego; California; United States; Bellingham; Wash.; SPIE; 2016 (Proceedings of SPIE; 9783); p. 97831A-1-97831A-9. ; ISBN 978-1-5106-0018-8; DOI: 10.1117/12.2216181.

Würfl, Tobias et al. "Deep Learning Computed Tomography" ECCV Conference 2016; Springer International Publishing AG; pp. 432-440; 2016.

Hahn, Juliane. et al.: "Cardiac Motion Compensation from Short-Scan CT Data: A Comparison of Three Algorithms. In Proceedings of the 4th International Conference on Image Formation in X-Ray Computed Tomography"; Siemens Healthcare GmbH 1. Power Point Präsentation; 2. publication Jul. 18-22, 2016. 2013. pp. 185-188.

Bhagalia, Roshni et al.: "Nonrigid registration-based coronary artery motion correction for cardiac computed tomography"; in: Med Phys.; vol. 39, No. 7; pp. 4245-4254; 2012;.

Hahn, Juliane et al.: "Motion compensation in the region of the coronary arteries based on partial angle reconstructions from short-scan CT data"; in: Medical Physics; vol. 44; No. 11; pp. 5795-5813; 2017; DOI: 10.1002/mp.12514.

Isola, A., A. et al.: "Cardiac motion-corrected iterative cone-beam CT reconstruction using a semi-automatic minimum cost path-based coronary centerline extraction": in: Computerized Medical Imaging and Graphics; vol. 36, pp. 215-226; 2012;.

Rohkohl Christopher et al., "Improving best-phase image quality in cardiac CT by motion correction with MAM optimization", in: Medical Physics, vol. 40, No. 3, Mar. 2013, pp. 031901-1 til 031901-15.

Kim, Seungeon et al.: "Cardiac motion correction based an partial angle reconstructed images in x-ray CT"; in: Med. Phys.; vol. 42, No. 5, pp. 2560-2571; May 2015; DOI: 10.1118/1.4918580.

Tang, Qiu Lin et al.: "Motion estimation and compensation for coronary artery and myocardium in cardiac CT"; in: Medical Imaging, San Diego; 2015.

European Search Report with Patent Application No. 18163687.9 dated Sep. 24, 2018.

* cited by examiner

METHOD FOR PROCESSING PARAMETERS OF A MACHINE LEARNING METHOD AND RECONSTRUCTION METHOD

PRIORITY STATEMENT

The present application hereby claims priority under 35 U.S.C. § 119 to European patent application number EP 18163687.9 filed Mar. 23, 2018, the entire contents of which are hereby incorporated herein by reference.

FIELD

Embodiments of the invention generally relate to a method for processing parameters of a machine-learning method for providing a correction dataset for motion correction of a CT image dataset of an object that moves during recording thereof; to a reconstruction method that uses the processed machine-learning method and/or to an apparatus.

BACKGROUND

With imaging via a computed tomography device (CT scanner), an X-ray source and/or a detector travel on a predefined trajectory, in particular on a circular or helical trajectory, relative to an object to be examined. Herein, a (CT) image dataset is recorded from different (recording) angles. In particular, in the field of medical diagnostics in which an organ of a patient such as, for example, the heart is examined, herein a recording time for the CT image dataset for the entire angular range to be recorded is comparatively long and so the organ, or at least a part of the organ, moves during the recording of the CT image dataset.

As a result, motion artifacts of the moving object are visible in a (reconstruction) image dataset reconstructed from the CT image dataset. The drawback is that such motion artifacts make reliable diagnosis difficult. Thus, motion artifacts represent an error source during diagnosis. For example, movement of the heart during the recording of the CT image dataset results in the structure of cardiac arteries being depicted as unclearly discernible, in particular blurred and/or deformed, in a reconstruction image dataset depicted as a pictorial representation (image).

Hardware-based options are known, such as, for example, the use of a second detector and a second X-ray source or increasing the rotational speed of a gantry bearing the X-ray source and the detector. However, such options are comparatively expensive.

Also known are methods which determine a correction dataset for the recorded CT image dataset in order to reduce motion artifacts. For example, "Motion compensation in the region of the coronary arteries based on partial angle reconstruction from short scan data" by J. Hahn et al. in "Medical Physics", 2017 November, Vol. 44(11), pp 5795-5813, the entire contents of which are incorporated herein by reference, discloses a known method for reducing motion artifacts in a reconstruction of coronary vessels. Herein, motion along a centerline of the corresponding coronary artery is modeled by way of a motion vector field the parameters of which are estimated by way of a cost function.

For example, a known method is further disclosed in "Nonrigid registration-based coronary artery motion correction for cardiac computed tomography" by R. Bhagalia et al. in "Medical Physics", 2012 July, Vol. 39(7), pp 4245-4254, the entire contents of which are incorporated herein by reference, that motion compensation for coronary vessels is achieved by way of three-dimensional deformation ("warping") of a series of partial reconstructions based on estimated motion vector fields.

Furthermore, "Cardiac motion corrected iterative cone-beam CT reconstruction using a semi-automatic minimum cost path-based coronary centerline extraction" by A. A. Isola et. al. in "Computerized medical imaging and graphics", 2012 April, Vol. 36(3), pp 215-226, the entire contents of which are incorporated herein by reference, discloses another known method that uses motion vector fields determined from a set of centerlines of the corresponding coronary vessels to obtain motion-artifact-free reconstructions of coronary vessels.

Common to all these methods is that an algorithm is used to determine a motion vector field as a correction dataset for the movement of the object during the recording of the CT image dataset. However, in particular due to the determination of the correction dataset by way of the respective algorithm, the methods are comparatively time-consuming and so a comparatively large amount of time passes between the recording of the CT image dataset and the provision of the motion-reduced reconstruction image dataset by way of the correction dataset for diagnosis.

The publication DE 10 2009 007 236 A1, the entire contents of which are incorporated herein by reference, discloses a method for scanning a moving examination object with a CT system in which data is acquired during a rotational movement of a transmitter/receiver pair around the examination object. Furthermore, sectional images of the examination object are ascertained from the data by way of an iterative algorithm, wherein motion information relating to the movement of the examination object is taken into account in the iterative algorithm during data acquisition.

The publication DE 10 2011 007 529 A1, the entire contents of which are incorporated herein by reference, discloses a method, a radiation therapy system and a combination of a CT system and a radiation therapy system for determining a motion profile of a moving object in an examination object with an emitter-detector system that can be displaced relative to the examination object, wherein the following method steps are carried out:

scanning the examination object in the region of the moving object during a displacement of the emitter-detector system relative to the examination object and generating a pixel dataset with attenuation values over time, removing stationary structures from the pixel dataset, determining an attenuation value induced by the moving object in each detector line at a plurality of successive time points of the scanning and forming a 3D dataset from the values from the attenuation peak of the detector lines from the detector lines and the scanning readout times, and determining at least one of the values from the following list from the results dataset: frequency and/or phase and/or amplitude of the movement of the object, location of the object during scanning, position of the object in a prespecified phase of the movement.

DE 10 2011 083 647 A1, the entire contents of which are incorporated herein by reference, discloses a method for generating a motion-compensated CT image dataset, wherein:

a projection dataset of a CT system comprising a prespecified moving phase and a projection angle range that enables the direct reconstruction of a CT image dataset is acquired, the motion field is determined iteratively by:
multiple reconstruction of the one CT image dataset with a first image resolution with a motion-compensating reconstruction method using a first analytical reconstruction algorithm and different motion fields in each case from a plurality of location-specific motion vectors,
and ascertaining the motion field using at least one prespecified constraint,
and reconstruction of a final CT image dataset with a second image resolution using a motion-compensating reconstruction method based on a second reconstruction algorithm and the ascertained motion field.

SUMMARY

At least one embodiment of the present application discloses a method that enables comparatively quick provision of a correction dataset for the corresponding CT image dataset. It is furthermore intended to disclose a reconstruction method for generating a reconstruction image dataset. Furthermore, it is intended to disclose an apparatus for carrying out one or both methods.

Advantageous developments and embodiments are the subject matter of the claims.

According to an expedient embodiment, a method for processing parameters of a machine-learning method for providing a correction dataset for motion correction of a CT image dataset of an object that moves during recording thereof, comprises:

providing a training dataset, including a number of reference image datasets for introduction into the machine-learning method;

performing iteration, wherein in each of a plurality of steps of the iteration, a correction dataset is determined for each of the number of reference image datasets via the machine-learning method, and a result of a cost function dependent on the correction dataset determined in each iteration step is ascertained; and terminating the performing of iterations, or altering a parameter of the machine-learning method, in dependence of the result of the cost function.

According to an expedient embodiment, a reconstruction method for generating a motion-corrected reconstruction image dataset for a CT image dataset of an object moving during recording, the reconstruction comprises:

acquiring the CT image dataset of the object, while moving, and providing the CT image dataset via a computed tomography device;

evaluating the CT image dataset via a machine-learning method;

providing a correction dataset corresponding to movement of the object as a result of the evaluating; and generating a motion-corrected reconstruction image dataset, from the correction dataset and the CT image dataset.

According to an expedient embodiment, an apparatus comprises a controller, which is provided and embodied to carry out the method in one of the embodiments and/or to carry out a reconstruction method of an embodiment.

According to an expedient embodiment, an apparatus comprises a controller configured to generate a motion-corrected reconstruction image dataset for a CT image dataset of an object moving during recording, generation of the motion-corrected reconstruction image dataset via the controller including:

acquiring the CT image dataset of the object, while moving, and providing the CT image dataset via a computed tomography device;

evaluating the CT image dataset via a machine-learning method;

providing a correction dataset corresponding to movement of the object as a result of the evaluating; and generating a motion-corrected reconstruction image dataset, from the correction dataset and the CT image dataset.

Expediently, another embodiment is directed to a computer-readable medium on which the machine-learning method is deposited.

BRIEF DESCRIPTION OF THE DRAWINGS

The following explains an example embodiment of the invention with reference to a drawing, wherein.

Corresponding parts are given the same reference characters in all the figures.

DETAILED DESCRIPTION OF THE EXAMPLE EMBODIMENTS

Figure 1:
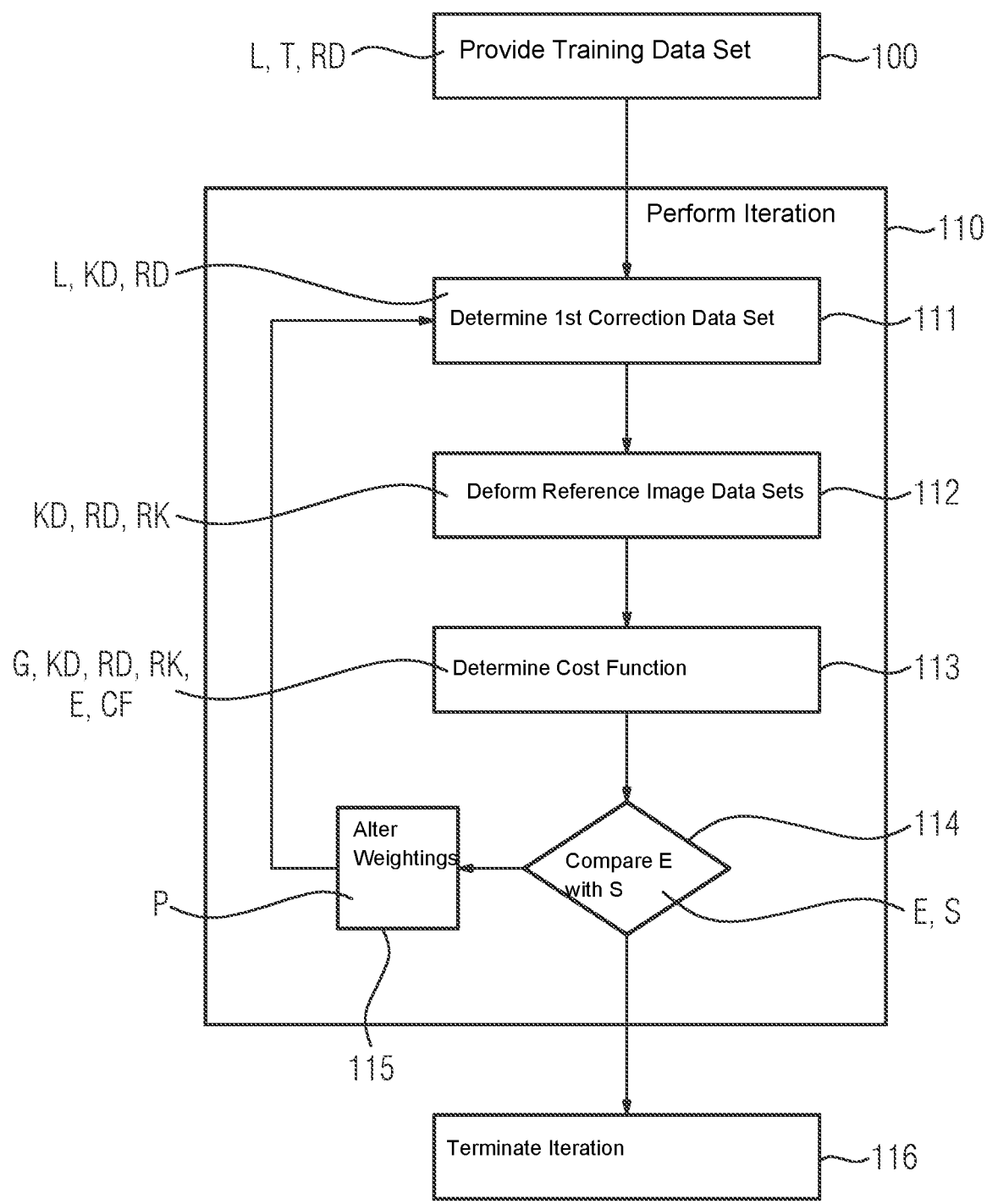
FIG. 1 shows a schematic flowchart of a method for processing parameters of a machine-learning method, in which an iteration is performed, wherein in each of the iteration steps thereof a result of a cost function is ascertained.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

To this end, parameters of a machine-learning method are processed in a method in at least one embodiment, wherein the machine-learning method is used to provide a correction dataset for motion correction of a CT image dataset of an object that moves during recording thereof. The processing of the parameters of the machine-learning method is also called training. Before commencing the training, the parameters are initialized, for example, with random numbers. The CT image dataset represents an intensity profile of the X-rays incident on a detector from different (recording) angles. The CT image dataset is in particular a so-called sinogram.

According to the method of at least one embodiment, first, a training dataset with a number of reference image datasets to be introduced (fed) into the machine-learning method is provided and introduced. In other words, the training dataset is supplied to the machine-learning method as an input dataset (input).

A reference image dataset can be a previously known CT image dataset provided to process the parameters of the machine-learning method. For example, clinical recordings of an object such as a heart or from recordings of a so-called phantom are used to this end. Alternatively, reference image datasets of this kind, can be, for example, generated by calculation or simulation of a moving object.

According to the method of at least one embodiment, furthermore, iteration is performed with at least one iteration step. In each of the iteration steps of the iteration, a correction dataset is determined for each of the reference image datasets via the machine-learning method and a result of a cost function ascertained. Herein, the cost function is dependent on the correction datasets determined in this iteration step.

A correction dataset is in particular embodied as a motion vector field representing a movement of the object in an image dataset.

The cost function is a mathematical function representing a deviation (difference) between variables or data ascertained via the machine-learning method (the prediction) and corresponding reference values or actual values. In other words, the cost function quantifies an error in the prediction of the machine-learning method. For example, the cost function is the mean-square deviation between the ascertained variables and the corresponding reference values.

The iteration is terminated or a parameter of the machine-learning method is altered in dependence on the result of the cost function. In particular, a threshold value is prespecified to this end. Therefore, the threshold value represents a maximum permissible error in the prediction made via the machine-learning method. If the threshold value is undershot by the result of the cost function, the iteration for the respective parameter is terminated, otherwise a further iteration step is performed with a different parameter. After the termination of the iteration, the iteration is performed for the next reference image dataset.

Particularly preferably, the parameter is altered such that the result of the cost function is reduced. In particular, the parameters are altered in accordance with the so-called "stochastic gradient descent" method. This reduces an error in a prediction determined via the machine-learning method with an altered parameter.

For example, the training dataset may or can be divided into partial training datasets. Then, an iteration is performed for each of the partial training datasets, wherein in each iteration step of the respective iteration, the parameters are processed in an analogous manner or the iteration of the respective partial training dataset is terminated in dependence on the result of the cost function. This is in particular advantageous when an apparatus carrying out the machine-learning method has only a comparatively small memory and thus it is not possible to take account of all the reference image datasets in one single iteration or this would result in a comparatively long processing time.

Herein, the machine-learning method of at least one embodiment, also called machine learning, is executed as a learning or prediction algorithm which is executed via a controller. After completion of a training phase with previously known training datasets, this machine-learning method advantageously recognizes patterns and regularities. Thus, there is no laborious learning or deposition or storage of the previously known reference image datasets in the fed-in training dataset and correction datasets intended for this purpose instead generalizations and/or relationships are determined.

For example, it is possible to use the machine-learning method, which is in particular embodied as a prediction algorithm, for assessment or evaluation of an unknown dataset. After completion of the training phase, it is thus possible via the trained machine-learning method to evaluate a fed-in dataset comparatively quickly and to output corresponding results of this evaluation, i.e. in this case a correction dataset for motion correction of a fed-in CT image dataset. When using such a machine-learning method for the provision of a correction dataset as the result of the evaluation of a CT image supplied thereto, this advantageously takes place in a comparatively short time. As a result, CT image datasets can be corrected and provided for a diagnosis comparatively quickly.

In a first variant embodiment of the method, the result of the cost function is determined using differences from the correction datasets and previously known training correction datasets. Herein, the training correction datasets are deposited in the training dataset and assigned to the corresponding reference image dataset. In particular, a mean value of the quadratic differences is used as the result of the cost function, however, alternatively the differences are used as arguments of a mathematical function. In this first variant embodiment, therefore, the training dataset comprises previously known training correction datasets each of which is assigned to the corresponding reference dataset. These training correction datasets have, for example, been ascertained via one of the methods named in the introduction, the entire contents of which are incorporated herein by reference, from the corresponding reference dataset or alternatively via a simulation of the reference dataset and the assigned training correction dataset.

In a second variant embodiment of the method, to ascertain the result of the cost function, first, each of the reference image datasets is deformed (adapted) according to the assigned and determined correction dataset, in particular, the intensity profile (intensity distribution) of the reference image dataset is altered in accordance with the determined correction dataset. For example, rigid or non-rigid known methods can be used to this end. Then, a reconstruction image dataset is created from each of the deformed reference image datasets. In particular a known reconstruction method, for example so-called filtered back-projection is used to create a pictorial representation (image) of the object as a reconstruction image dataset. Alternatively, the reconstruction image dataset is, for example, a deformed sinogram.

For example, the cost function can be determined via the reconstruction image datasets. To this end, these are, for example, compared with training reconstruction image datasets deposited in the training dataset and assigned to the corresponding reference image datasets. Similarly to the first variant, these training reconstruction image datasets have, for example, been ascertained via one of the methods named in the introduction, the entire contents of which are incorporated herein by reference, from the corresponding reference dataset. Similarly, here, differences from the determined reconstruction datasets and previously known training reconstruction datasets are used to determine the result of the cost function.

Alternatively, according to an advantageous development of at least one embodiment, a variable dependent on the movement of the object is ascertained from the reconstruction image datasets and used to determine the result of the cost function. For example, a mean value of the variables determined from the reconstruction image datasets is used as the result. Herein, therefore, only reference datasets are used but no further datasets assigned to these reference datasets. As an alternative to this variable, a restriction to positive values (positivity constraint) of the reference datasets deformed via the correction datasets is used as a cost function.

In one suitable development, an entropy is determined from the corresponding reconstruction image dataset or of a selected part thereof and used as the variable ascertained from the reconstruction image dataset. If the reconstruction image dataset is embodied as an image, it is expedient to select the region of the image relevant for diagnosis (region of interest) as the part of the image.

Alternatively or additionally to entropy, an entropy gradient and/or the above-described restriction to positive values are used as the variable ascertained from the reconstruction image dataset.

According to a particularly suitable embodiment of the method an (artificial) neural network, in particular a convolutional neural network (CNN) is used as the machine-learning method. Herein, a neural network comprises an input layer into which datasets are fed, at least one hidden layer and an output layer. Herein, the network or the layers each comprise a number of so-called neurons, which are interconnected. Each of the connections further comprises a weighting that determines the influence of a respective transmit neuron on the corresponding target neuron (receive neuron), wherein the individual neurons are, for example, defined as a mathematical function. The parameters processed via the method are in particular the weightings. During the course of the processing of the parameters, in particular a plurality of weightings is altered in one step, wherein the parameters are suitably altered such that an error in the prediction or the error in an evaluation decreases and thus the result of the cost function is reduced as a result of the alteration of the parameters. For example, the weightings are altered in accordance with the so-called "gradient descent" method or the so-called "stochastic gradient descent" method.

A convolutional neural network (CNN) is in particular suitable for evaluating image datasets. For example, an alternative is to use a neural network with fully connected neuron layers (FCN), wherein, however, a convolutional neural network comprises comparatively few parameters compared to a neural network with fully connected neuron layers and hence the computational effort of the convolutional neural networks is comparatively low.

The previously known reference image datasets are integrated in the neural network as a result of the training. The advantage of a neural network in particular resides in the fact that it is also able to learn and work without instruction. The reference image datasets that are previously known via the training and the correction datasets corresponding to movements of the object are integrated in the topology of the neural network, i.e. the structure of the neural network and the interconnections of the neurons, so that, when a data set for evaluation is fed in, it is examined for previously known features.

In one reconstruction method example embodiment for generating a motion-corrected reconstruction image dataset for a CT image dataset of an object that moves during recording thereof, in a first step, a CT image dataset of a moving object is acquired and provided via a computed tomography device.

In a subsequent second step, the CT image dataset is evaluated via a machine-learning method, which was in particular trained according to a method in one of the above-described variants.

A correction dataset corresponding to the movement of the object is provided as the result of the evaluation. The correction dataset and the CT image dataset are used to generate a motion-corrected reconstruction image dataset. To this end, the CT image dataset is deformed in accordance with the correction dataset. Alternatively, the correction dataset is used as initial dataset for an iterative determination via a known method, for example, one of the methods described in the introduction that are incorporated herein by reference, so that the duration of this method is reduced. To summarize, therefore, due to the use of a machine-learning method, in particular embodied as a neural network, the provision of the motion-corrected reconstruction dataset takes place comparatively quickly.

For example, the machine-learning method can additionally be further trained via this CT image dataset and, if appropriate, via the correction dataset.

According to an expedient embodiment, an apparatus comprises a controller, which is provided and embodied to carry out the method in one of the above-presented variants and/or to carry out the reconstruction method. Expediently, the apparatus further comprises a computer-readable medium on which the machine-learning method is deposited.

FIG. 1 is a schematic flowchart of a method for processing parameters P of a machine-learning method L for providing a correction dataset KD for motion correction of a CT image dataset CB of an object 2 that moves during recording thereof.

In a first step, introduction 100, according to the method a training dataset T with a number of reference image datasets RD is provided and introduced into the machine-learning method L. In a subsequent second step, iteration 110 is performed. Herein, the iteration 110 includes at least one iteration step.

In each of the iteration steps of the iteration 110, first a correction dataset KD is determined for each of the reference image datasets RD via the machine-learning method L embodied as an (artificial) neural network (step 111). The reference image datasets RD are then deformed via the respective correction datasets KD in a step 112 and in each case, a (motion-)corrected reconstruction image dataset RK is created from the deformed reference image datasets RD.

Furthermore, in a further step 113 a result E of a cost function CF is determined. The cost function is dependent on the correction datasets KD determined in this iteration step. To this end, in each case a variable G is ascertained from the reconstruction image datasets RK created via the correction datasets KD and the reference image datasets RD and used to determine the result E of the cost function CF. Herein, the variable G is an entropy of a from the corresponding reconstruction image dataset RK, for example, the entropy of an image ascertained via filtered back-projection from the deformed reference image dataset RD. Here, a mean value of the variables G determined from the reconstruction image datasets RK is used as the result E of the cost function CF.

In a comparison step 114, this result E is compared with a, in particular prespecified, threshold value S. Herein, the threshold value S serves to limit a maximum permissible error or a maximum permissible deviation of a prediction made via the machine-learning method L. If the result E is higher than the threshold value S, i.e. the deviation or the error is too high, parameters P, here weightings of the neural network, are altered (step 115). The weightings P of the neural network L are altered in accordance with the so-called "stochastic gradient descent" method. However, if the result E undershoots the threshold value S, the iteration 110 is terminated (step 116). This is the manner in which the parameters P of the machine-learning method L and the topology of the neural network are processed.

Figure 2:
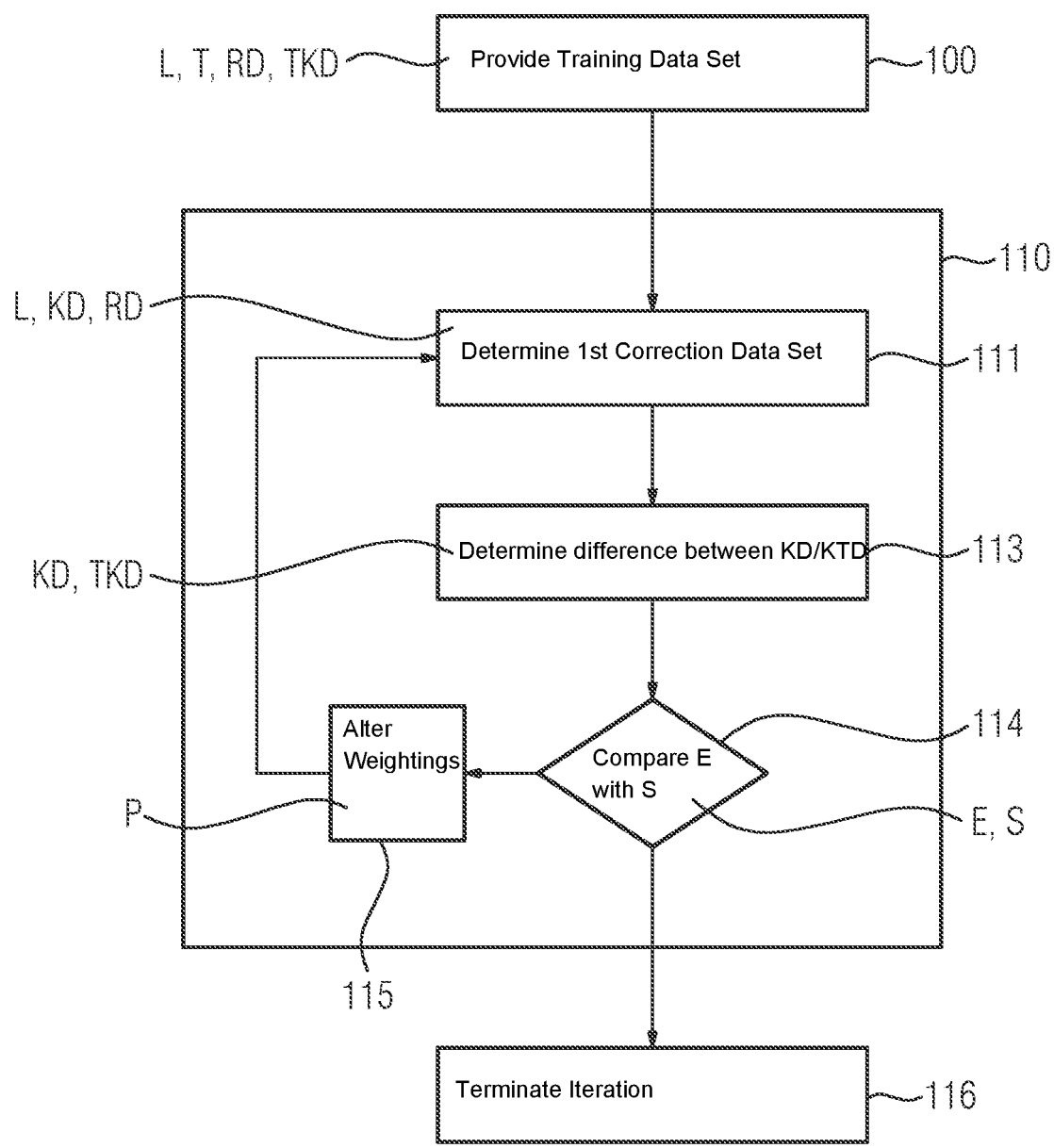
FIG. 2 shows a schematic flowchart of an alternative embodiment of the method in FIG. 1 with an alternative determination of the result of the cost function.

FIG. 2 shows an alternative embodiment of the method. This alternative embodiment differs from the variant shown in FIG. 1 in that, in addition to the reference image datasets RD, the training dataset TD comprises the training correction dataset TKD assigned to the corresponding reference image dataset RD. In step 113, in each case a difference between the corresponding datasets KD and TKD is determined from the correction datasets KD determined in step 111 and the assigned training correction dataset TKD and used to determine the result E of the cost function. Here, the mean value of the squared differences is used as the result E of the cost function CF.

Therefore, step 112 is not performed in the variant in FIG. 2. The other steps of the method, in particular the termination of the iteration 110 in the event of the threshold value S being undershot by the result E of the cost function CF (step 116), or alternatively the alteration of the parameters P (step 115), are performed analogously.

Figure 3:
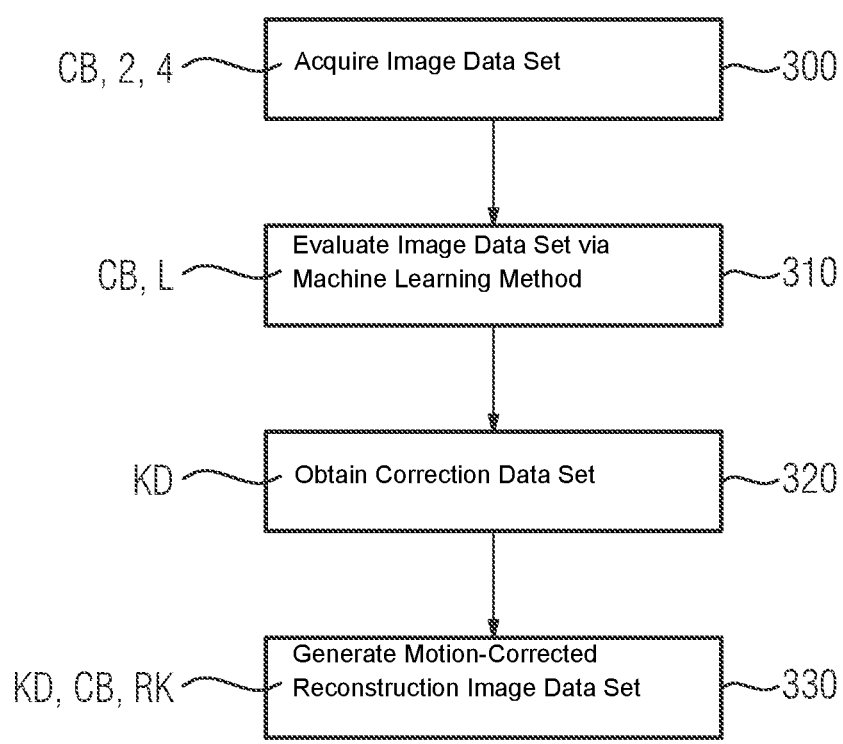
FIG. 3 shows a schematic flowchart of a reconstruction method for generating a motion-corrected reconstruction image dataset for a CT image dataset.

FIG. 3 depicts a reconstruction method for generating a motion-corrected reconstruction image dataset RK for a CT image dataset CB of an object 2 that moves during recording thereof. Herein, in a first step 300, the CT image dataset CB of the moving object 2 is acquired and provided via a computed tomography device 4.

Figure 4:
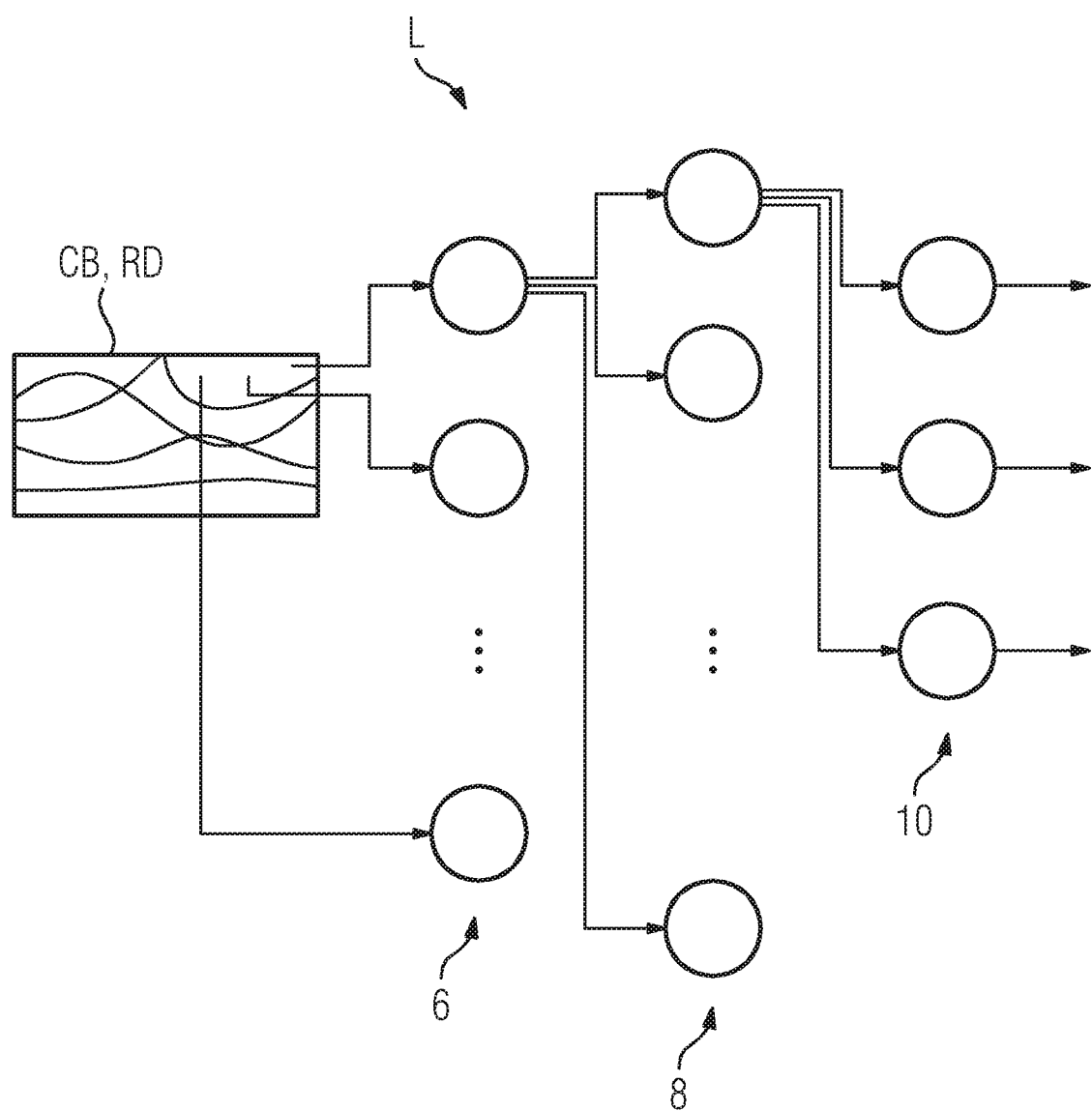
FIG. 4 shows a neural network for carrying out a machine-learning method.

In a subsequent second step 310, the CT image dataset CB is evaluated via the machine-learning method L (FIG. 4). The machine-learning method has been trained in accordance with one of the methods in FIG. 1 or FIG. 2.

A correction dataset KD corresponding to the movement of the object 2 is provided as the result of the evaluation (step 320). This and the CT image dataset CB are used to generate a motion-corrected reconstruction image dataset RK in a step 330. To this end, the CT image dataset CB is deformed in accordance with the correction dataset KD, i.e. the CT image dataset CB is altered in accordance with the correction dataset KD determined. In this way, the movement of the object 2 during recording of the CT image dataset CB is corrected and motion artifacts are avoided in the reconstruction image dataset RK embodied as an image. As a result, errors are avoided in an interpretation or diagnosis based on the image, which is now motion-corrected.

FIG. 4 is a schematic and greatly simplified depiction of a neural network L used in the methods in FIG. 1 to FIG. 3. The neural network L comprises an input layer 6 into which datasets are fed, at least one hidden layer 8 and an output layer 10. The layers 6, 8 and 10 in turn include in each case a number of neurons, which are not described further, which are interconnected and in each case defined as a mathematical function. For the purposes of a better overview, herein by way of example FIG. 4 only shows nine connections to neurons, but in this embodiment, the neurons in the input layer 6 are in each case connected to all the neurons of the hidden layer 8 and the neurons of hidden layer 8 are in each case connected to all the neurons of the output layer 10. Herein, each of these connections has a weighting P, which determines the influence of a respective transmit neuron on the corresponding target neuron.

The input layer 6 with a number of neurons is determined from the CT image dataset CB or, during the training phase, from the reference image datasets RD. Herein, for example, each pixel or in each case a matrix of pixels of the image data set fed-in in the form of a sinogram corresponds to a neuron of the input layer 6.

The features of a movement of the object 2 in the reference image data RD are integrated in mathematical functions and/or weightings of the neurons of the neural network. In other words, the neural network is trained in the motion features of the reference image data RD and these are integrated in its topology (FIG. 4). In this way, the at least one hidden layer 8 extracts and identifies characteristic motion features of the supplied dataset. Hence, in an evaluation of a fed-in dataset, a movement is identified and the corresponding correction dataset KD output as the result E to the (output) neurons of the output layer 10 for the correction of these motion features.

Figure 5:
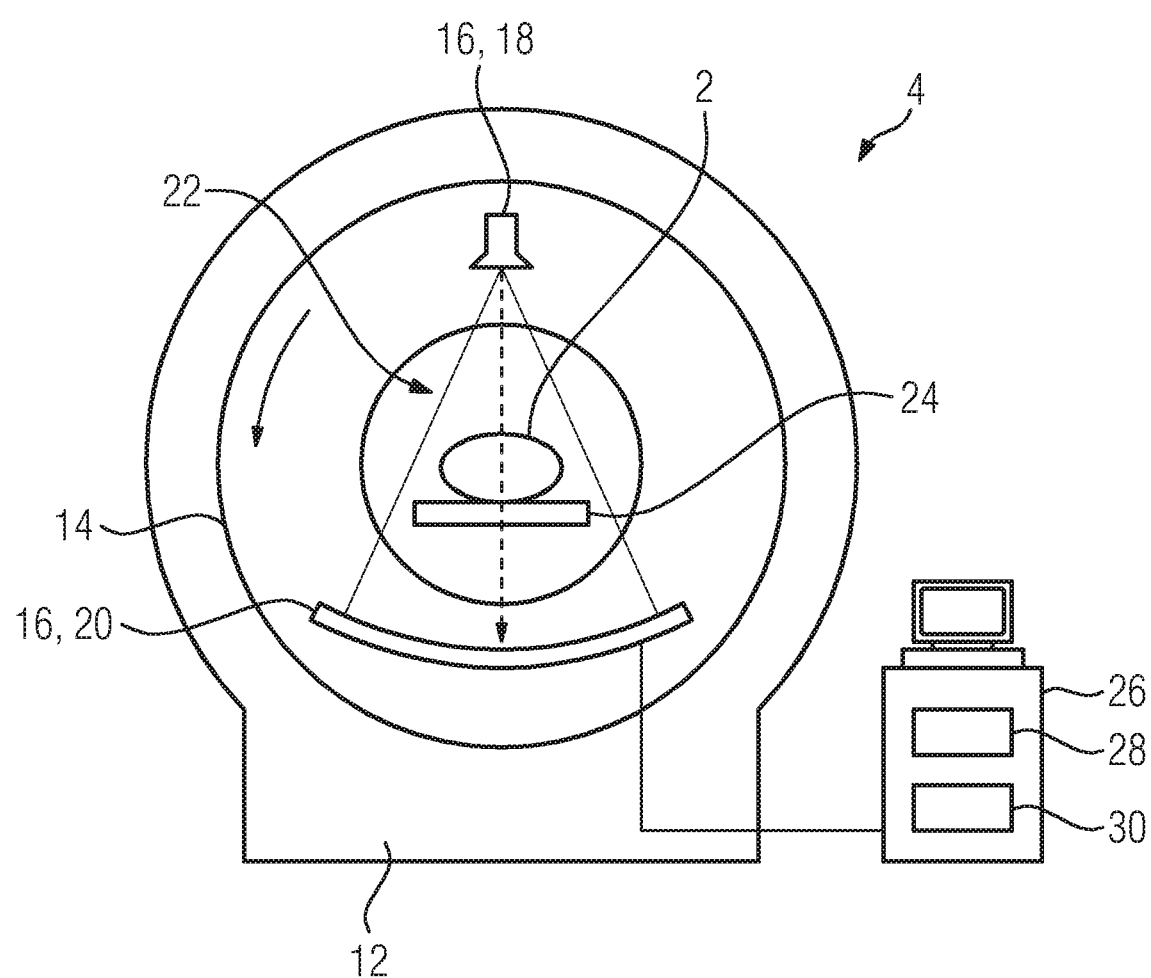
FIG. 5 shows a schematic front view of a computed tomography device connected to an apparatus embodied as a computer, wherein the apparatus comprises a controller.

FIG. 5 shows a computed tomography device 4. This has a retaining frame 12 for an annular gantry 14. Herein, the gantry 14 is mounted rotatably on the retaining frame 12. The gantry 14 bears an X-ray system 16 with an X-ray source 18 for the generation of X-rays and with an (X-ray) detector 20 for the X-rays arranged opposite thereto in. A patient bench 24 can be introduced or moved into the tunnel-shaped receiving region 22 formed via the annular gantry 14. For recording a CT image dataset, the object to be examined 2, in particular a patient, is placed on the patient bench 22 and moved into the receiving region 22. On rotation of the gantry 14, X-ray system 10 travels around the object 2 on the patient bench 24 in a circular trajectory. As a result, a CT image dataset CB of the object 2 is recorded from different (spatial, recording) angles, wherein the CT image dataset CB represents an intensity profile of the incident X-rays according to the different (recording) angles.

To acquire the CT image dataset CB recorded (acquired) via the detector 20, the latter is connected to an apparatus 26 embodied as a reconstruction computer via signal transmission technology. This comprises a controller 28 for carrying out the method shown in FIG. 1 or FIG. 2 and the reconstruction method shown in FIG. 3 and a computer-readable medium 30 embodied as a hard disk on which the machine-learning method L embodied as a neural network in FIG. 1 to FIG. 4 is deposited.

The invention is not limited to the example embodiments described above. Rather, other variants of the invention can be derived therefrom by the person skilled in the art without departing from the subject matter of the invention. In particular, furthermore all the individual features described in connection with the example embodiments can also be combined with one another in another manner without departing from the subject matter of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for processing parameters of a machine-learning method for providing a correction dataset for motion correction of a CT image dataset of an object that moves during recording thereof, the method comprising:
   providing a training dataset, including a number of reference image datasets for introduction into the machine-learning method;
   performing iteration, wherein in each of a plurality of steps of the iteration, a correction dataset is determined for each of the number of reference image datasets via the machine-learning method, and a result of a cost function, that quantifies an error prediction of the machine-learning method, dependent on the correction dataset determined in each iteration step is ascertained; and
   terminating the performing of iterations when the cost function is below a threshold value and altering a parameter of the machine-learning method when the cost function is above the threshold function, in dependence of the result of the cost function, wherein, to determine the result of the cost function, each of the reference image datasets is deformed in accordance with an assigned correction dataset and a reconstruction image dataset is created from the reference image dataset deformed, wherein a variable dependent on movement of the object is ascertained from the reconstruction image datasets and is used to determine the result of the cost function, and wherein an entropy is determined from the reconstruction image dataset or of a selected part thereof, and is used as the variable ascertained from the reconstruction image dataset.

2. The method of claim 1, wherein, to determine the result of the cost function, differences from the correction datasets determined and previously known training correction datasets are used, wherein the training correction datasets are deposited in the training dataset and assigned to corresponding reference image datasets.

3. The method of claim 2, wherein, to determine the result of the cost function, each of the reference image datasets is deformed in accordance with an assigned correction dataset and the reconstruction image dataset is created from the reference image dataset deformed.

4. The method of claim 3, wherein a variable dependent on movement of the object is ascertained from the reconstruction image datasets and is used to determine the result of the cost function.

5. The method of claim 4, wherein an entropy is determined from the reconstruction image dataset or of a selected part thereof, and is used as the variable ascertained from the reconstruction image dataset.

6. The method of claim 2, wherein a neural network is used as the machine-learning method.

7. The method of claim 6, wherein the neural network is a convolutional neural network.

8. The method of claim 1, wherein a neural network is used as the machine-learning method.

9. The method of claim 8, wherein the neural network is a convolutional neural network.

10. A reconstruction method for generating a motion-corrected reconstruction image dataset for a CT image dataset of an object moving during recording, the reconstruction comprising:

acquiring the CT image dataset of the object, while moving, and providing the CT image dataset via a computed tomography device;

evaluating the CT image dataset via a machine-learning method, trained via the method of claim 1;

providing a correction dataset corresponding to movement of the object as a result of the evaluating; and generating a motion-corrected reconstruction image dataset, from the correction dataset and the CT image dataset.

11. An apparatus, comprising:

a controller configured to generate a motion-corrected reconstruction image dataset for a CT image dataset of an object moving during recording, generation of the motion-corrected reconstruction image dataset via the controller including:

acquiring the CT image dataset of the object, while moving, and providing the CT image dataset via a computed tomography device;

evaluating the CT image dataset via a machine-learning method that includes performing iteration processing of the image dataset, wherein in a iteration, a correction dataset is determined for each of the number of reference image datasets, and a result of a cost function, that quantifies an error prediction, dependent on the correction dataset determined in each iteration step is ascertained, and terminating the iteration processing when the cost function is below a threshold value and altering a parameter of the machine-learning method when the cost function is above the threshold function, in dependence of the result of the cost function;

providing a correction dataset corresponding to movement of the object as a result of the evaluating; and generating a motion-corrected reconstruction image dataset, from the correction dataset and the CT image dataset, wherein, to determine the result of the cost function, each of the reference image datasets is deformed in accordance with an assigned correction dataset and a reconstruction image dataset is created from the reference image dataset deformed, wherein a variable dependent on movement of the object is ascertained from the reconstruction image datasets and is used to determine the result of the cost function, and wherein an entropy is determined from the reconstruction image dataset or of a selected part thereof, and is used as the variable ascertained from the reconstruction image dataset.

* * * * *